(12) United States Patent
Weidele

(10) Patent No.: US 7,781,194 B2
(45) Date of Patent: Aug. 24, 2010

(54) METHOD FOR USING BIOMASS IN BIOGAS PROCESS

(75) Inventor: Thomas Weidele, Kochstrasse 66, D-04275 Leipzig (DE)

(73) Assignees: KWK GbR, Leipzig (DE); Bernhard Krieg, Leipzig (DE); Thomas Weidele, Leipzig (DE); Rüdiger König, Leipzig (DE)

( * ) Notice: Subject to any disclaimer, the term of this patent is extended or adjusted under 35 U.S.C. 154(b) by 195 days.

(21) Appl. No.: 11/992,970

(22) PCT Filed: Sep. 15, 2006

(86) PCT No.: PCT/EP2006/008995

§ 371 (c)(1), (2), (4) Date: May 9, 2008

(87) PCT Pub. No.: WO2007/039067

PCT Pub. Date: Apr. 12, 2007

(65) Prior Publication Data

US 2009/0035834 A1 Feb. 5, 2009

(30) Foreign Application Priority Data

Sep. 30, 2005 (DE) ........................ 10 2005 047 719

(51) Int. Cl.
*C12P 5/00* (2006.01)
*C12P 5/02* (2006.01)
*C02F 3/00* (2006.01)

(52) U.S. Cl. ........................ 435/166; 210/603; 210/606; 435/140; 435/167

(58) Field of Classification Search ........................ None
See application file for complete search history.

(56) References Cited

U.S. PATENT DOCUMENTS

| 3,284,991 | A | 11/1966 | Ploeger et al. | |
|---|---|---|---|---|
| 6,569,332 | B2 * | 5/2003 | Ainsworth et al. | 210/603 |
| 7,563,371 | B2 * | 7/2009 | McCune-Sanders et al. | 210/603 |
| 2005/0145552 | A1 | 7/2005 | Sheets | |

FOREIGN PATENT DOCUMENTS

| DE | 4407564 | 9/1995 |
|---|---|---|
| DE | 19547320 | 6/1997 |
| DE | 19652127 | 6/1998 |
| GB | 2403164 | 12/2004 |
| WO | WO8001922 | 9/1980 |
| WO | WO03004217 | 5/2003 |
| WO | 2005049495 | 6/2005 |
| WO | 2007115660 | 10/2007 |

OTHER PUBLICATIONS

ROMPP Lexikon pp. 4734-4737—1999.

* cited by examiner

*Primary Examiner*—Herbert J. Lilling
(74) *Attorney, Agent, or Firm*—Horst M. Kasper

(57) ABSTRACT

The invention relates to a method for using biomass in a biogas process. The aim of the invention is to use substrates having a high nitrogen and solid content, and which using a small amount of water, has very good energy balance and is particularly environmentally friendly. Said aim is achieved by the virtue of the fact that the substrate is treated with a recirculated product in order to form a pumpable medium, and additionally treated with bacteria in cyclones and fermenters, which simultaneously removes the nitrogen in a stripping process, separates the solid fermentation radicals and further uses the recirculated product as a heat-exchanger and reaction medium. Said process is environmentally friendly and has a very good energy balance.

13 Claims, 4 Drawing Sheets

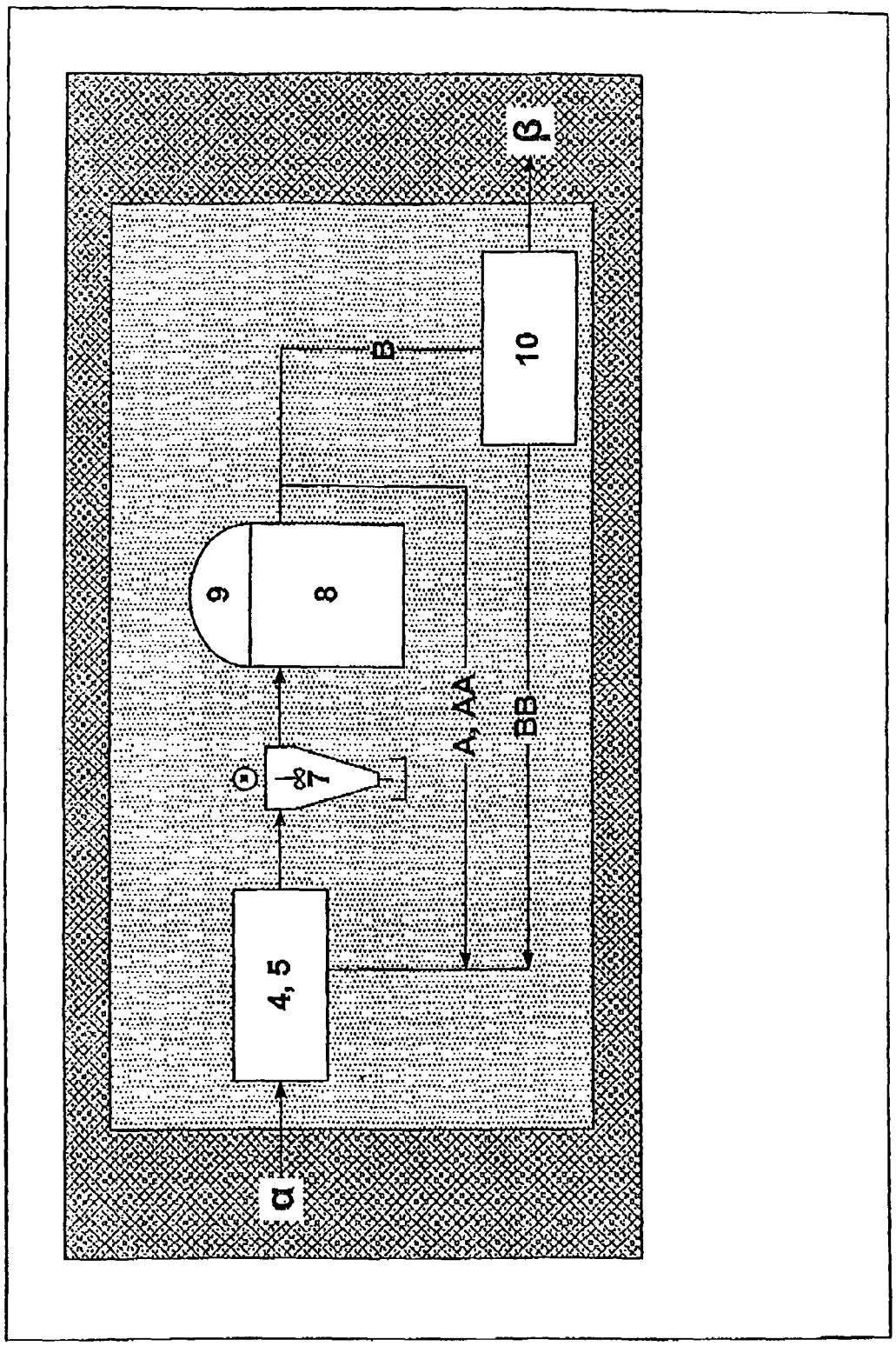
Fig. 1 Principal sketch

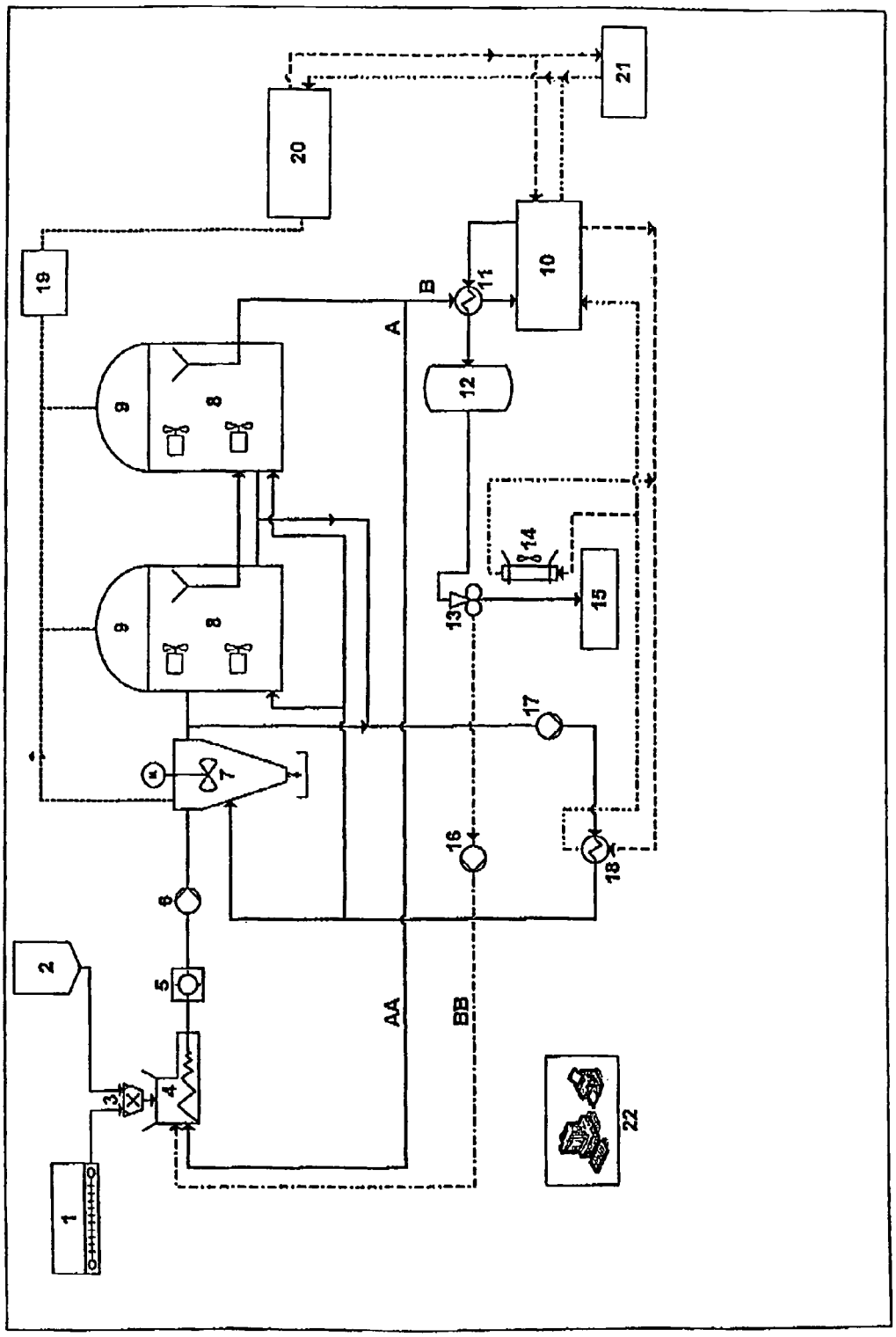
Fig. 2 Flow chart

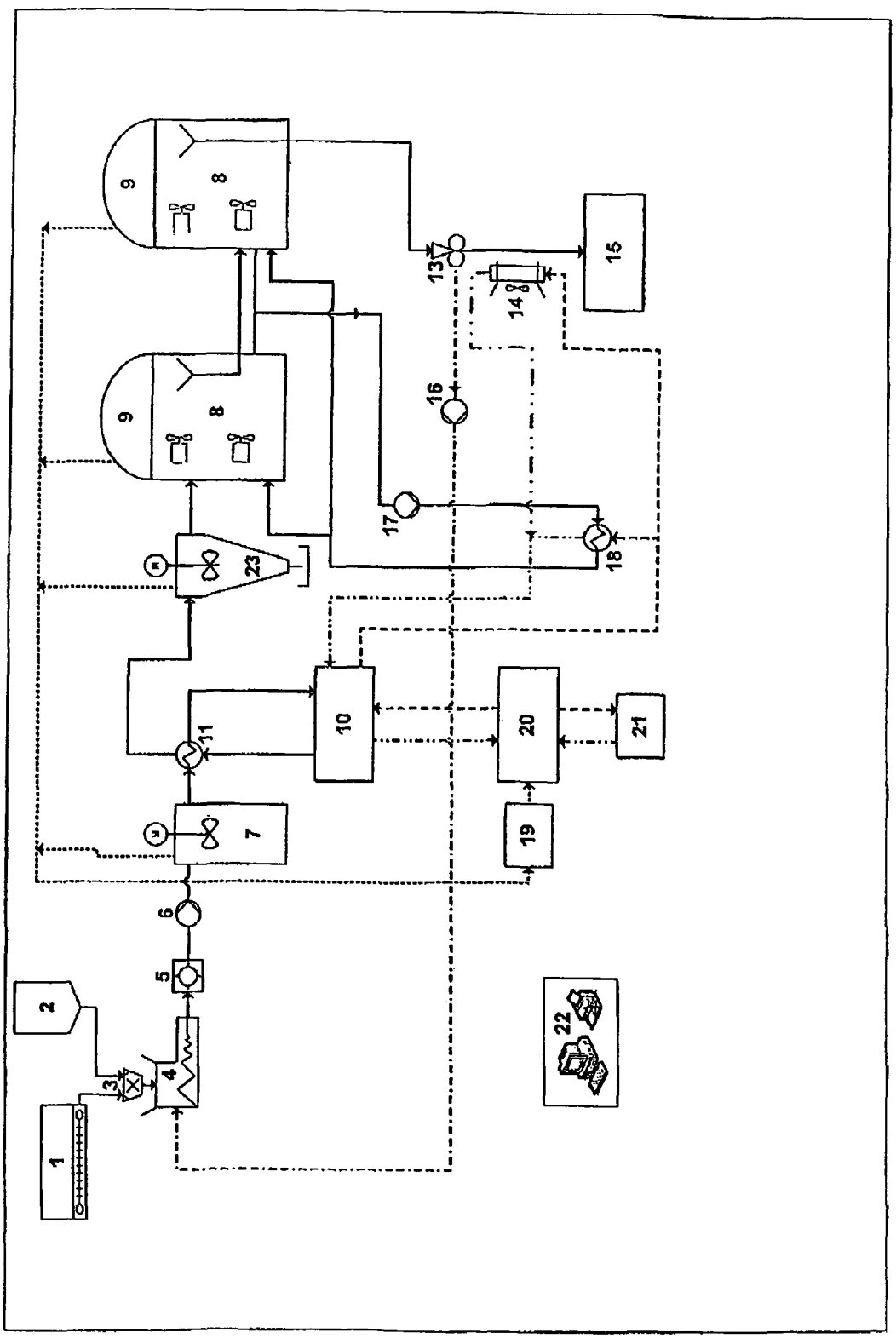
Fig. 3 Flow chart 2

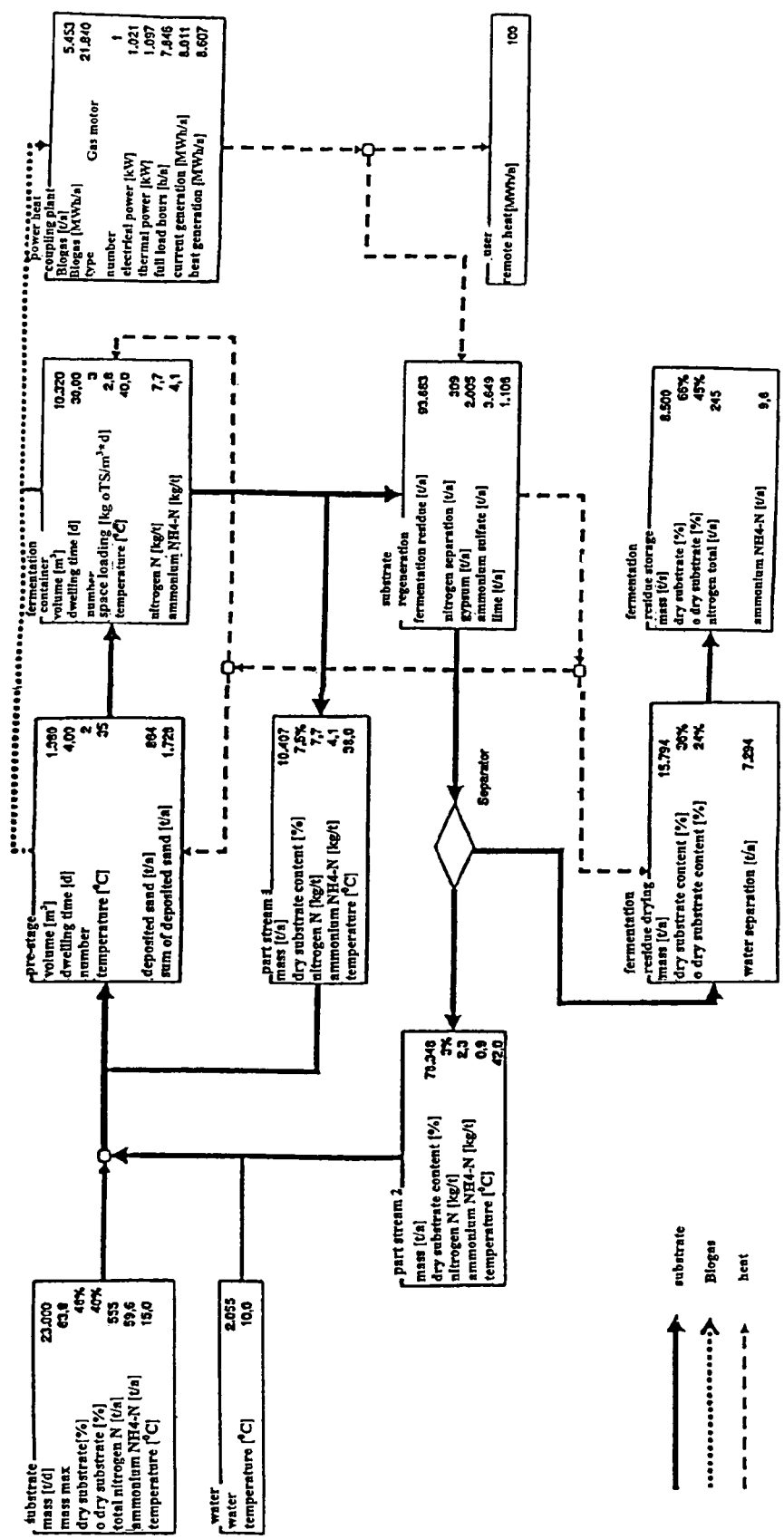
Fig. 4 Accounting Representation Embodiment

METHOD FOR USING BIOMASS IN BIOGAS PROCESS

The invention relates to a method for energetical utilization of biomass with high solid- and nitrogen parts as a substrate in biogas plants.

Table 1 shows by way of example several of these substrates. Further substrates with high solid parts are amongst others green cuttings of all kinds as well as garden and food waste. Furthermore, there exist substrates with very high nitrogen part such as coarse oil meals and slops. Substrates with high parts of foreign materials are for example chicken dung with a high part of lime and sand.

TABLE 1

Composition of selected substrates

| | Dry Substance [%] | | Substrate with high |
|---|---|---|---|
| | From | To | Nitrogen part |
| Pork liquid manure | 4 | 6 | x |
| Bovine liquid manure | 7 | 10 | |
| Bovine dung | 20 | 30 | |
| Corn silage | 27 | 35 | |
| Grass silage | 35 | 40 | x |
| Whole plant silage | 35 | 40 | x |
| Poultry dung | 35 | 75 | x |
| Cereals | 85 | 90 | x |

Table 1: composition of selected substrates

The known biogas methods are generally subdivided into dry fermentation process and wet fermentation process. The basis for an advantageous biogas process is amongst others an optimum disintegration of the substrate employed in order to furnish an attack surface as large as possible to the bacteria employed. The environmental conditions for the bacteria are of particular importance. The bacteria require a uniform temperature equalization of the process and a carrier medium, which allows a high mobility of the bacteria or, respectively, assures a feeding of the biomass to the bacteria. The temperature equalization is expensive, the necessary contacting defined within narrow limits between bacteria and substrate is cost intensive.

The substrates is usually comminuted and enclosed into an airtight container in solid form into dry fermentation process, wherein the biogas process runs in the airtight container. The usually low yield of biogas, which is caused by the non-uniform heat input and therewith the non-uniform temperature distribution and the low mobility of the bacteria.

These essential disadvantages are not present with the wet fermentation. Both a uniform process temperature as well as the mobility of the bacteria for, respectively, the feeding of the substrate are assured by the liquid carrier medium.

However, it is a disadvantage associated with the wet fermentation that substrates with high dry substance parts continuously have to be mashed with a liquid. This leads to an increase of the fermentation residual mass with corresponding logistic expenditures associated with storage and transport. The recirculation of fermentation residues for mashing offers a possibility to reduce the liquid requirements. This solution does however not work when substrates are employed with high nitrogen concentrations. For reducing the nitrogen concentrations there remains only the possibility of thinning with liquid.

If only water and not liquid manure is available for mashing, then there exists furthermore the danger for the process that the required bacteria are washed out and thereby an interruption in biogas production occurs. The possible washing out of the bacteria from the biogas process is caused by the long generation time of the bacteria, this means that more bacteria leave the fermenter with the fermentation residue than are newly formed. This holds in particular for the methane forming bacteria.

In connection with the recirculation of fermentation residues for mashing the substrate there occurs frequently an upward concentration of minerals in the fermenter. These minerals have partly the property of retarding materials relative to the biogas process.

A very problematic retarding material is ammonia. The recirculation of fermentation residues is critical in particular when employing substrates with high parts of nitrogen. The organically bound nitrogen is transformed into ammonium in the biogas process, wherein ammonium again stands in a chemical equilibrium with ammonia. This equilibrium depends essentially on the temperature and on the pH value. The ammonia is poison for the bacteria and is the cause of the so-called nitrogen retardation. The ammonium concentrated by the recirculation and the increased formation of ammonia interfere with the biogas generation process and in an extreme case can lead to a break off of the biogas formation. A continuous formation of ammonia occurs furthermore in the storage of the liquid fermentation residue based on the high ammonium concentrations and the formation of ammonia leads to ammonia emissions.

Large part foreign materials are usually deposited prior to the entry into the biogas plant. In contrast, small part foreign materials pass with the substrate into the fermenter and lead there to deposits. Especially the deposition of mud and sand represents a big problem. The cause for the deposition of foreign materials in the fermentation container is on the one hand the size of the foreign materials, which does not enable a separation with sieves or rakes. Furthermore the foreign materials are usually nonmagnetic and electrically neutral. A separation by gravity is frequently not possible, since the foreign materials are bound to the biomass and thus the difference in density relative to water or, respectively, to the mashed biomass is too low. Furthermore, the deposits in the fermentation container are also problematical, since the present automatic withdrawal systems such as slider or scraping floor function only insufficiently. The cause to the situation is that the deposits are whirled up by the slider and therefore remain to a large part in the fermentation container. The enrichment of the deposits leads then to an overloading of the withdrawal systems up to the failure and there remains only the manual withdrawal of the deposits, wherein the operation of the biogas plant has to be discontinued.

It is an object of the present invention to overcome the existing disadvantages of the biogas generation process and to use substrates with high solid parts and nitrogen parts energetically advantageous in a biogas plant. Here it is to be assured that the following points are realized:
  increase of the biogas production by
    separation of interfering materials
    optimization of the biology
    reducing the retarding materials (in particular the avoidance of enrichment of nitrogen in biogas plants);
  substantial savings in water;
  advantageous energy regime;
  avoidance of ammonia emissions;
  reducing the production of fermentation residues.

It is an object of the present invention to secure the biogas process in regular operation essentially without continuous addition of liquid. The fermentation residues amount can therewith be reduced. The fermentation residue is to be hygienized at the end of the process and shall be characterized by only small emissions (as for example ammonia).

Furthermore biomass with high parts in foreign materials shall be useful.

The invention is to solve furthermore the object, to use substrates with high solid parts for biogas production. In addition, the employment of nitrogen containing substrates (compare table 1) is to be possible.

The energy household of the complete process is to be created such that a technical, economic, and ecologically acceptable result is obtained with only small losses in heat.

The object is resolved according to the present invention in the main claim. The subclaims serve advantageous embodiments. The drawings serve to help understand the invention.

The method according to the present invention runs in detail as follows:

The biomass (substrate) is entered (1,2) as a solid material into the course of the process. The solid materials are comminuted (3) in order to enable an optimum biogas process. No liquid is fed to the invention with the exception of start-up processes. The biogas process proceeds in a pumpable/liquid state of the substrates. The comminuted substrates are mashed with recirculation liquid in a mixer (4). The substrates are again reduced in their size by an in-line comminuting machine (5) after the mixer, in order to increase the active surface, and are further transported with a pump (6).

The recirculation liquid is substituted by water or liquid manure only in the start-up phase of the invention process.

The hydrolysis and the acid formation as well as the separation of interfering materials are performed in the pre-stage, wherein the pre-stage is formed as a cyclone (7). The hydrolysis and the acid formation are the first disintegration stages in the biogas process. A separation of organic and inorganic components of the substrate occurs by the beginning of the biological disintegration. The heavier inorganic components, for example sand, are separated by the cyclone and do not interfere any longer with the further biogas process. The dwelling time of the substrate in the pre-stage amounts to up to six days. At the same time an optimization of the biogas process is accomplished by the spacial separation of the different disintegration stages, whereby in each case the optimum milieu conditions can be set for the specific bacteria. The formation of acetic acid and the generation of methane, that is the formation of the biogas, run in the thereto following fermentation containers (8,9). The fermentation of the substrates occurs thus mesophilic, that is at temperatures from 38 to 42 degrees centigrade, or thermophilic, that is at temperatures from 50 to 60 degrees centigrade. The dwelling time in the fermentation containers amounts to between 20 and 40 days. The number and the size of the fermentation containers as well as the dwelling time of the substrate mixture are depending on the kind and amount of the substrates.

The biogas is stored in gas bubbles (9) and after a cleaning (19) is transformed in electrical power and heat in the power heat coupling plant (20). Usually block heat power stations are employed, however also micro-gas turbines, gas turbines, fuel cells or ORC-processes can be employed.

The fermentation residue of the biogas process is employed for mashing the substrates in the mixer (4). Here the fermentation residue is separated in two partial streams.

Partial stream 1 (A) is untreated fermentation residue. The new substrate is biologically vaccinated through the untreated fermentation residue, which supports the friction-less course of the biogas process. This is associated with the large advantage that bacteria are brought into the mashing apparatus, wherein the bacteria particularly good correspond to the hitherto employed substrate, wherein the bacteria rapidly disintegrate the substrate and advance a high biogas production.

Partial stream 2 (B) is first subjected to a substrate preparation (10), in order to remove the retarding materials. Primarily concerned is here the removal of ammonium/ammonia with the aid of a stripping process. The stripping process is heated with the waste heat of the power heat coupling plant (20). At the same time a hygienization of the fermentation residue is achieved, that is the temperature during the stripping process is disposed above 70 degrees centigrade for time period of more than 60 minutes. For this reason, the stripping process operates in a batch operation. The separation degree of the ammonium nitrogen is to lie at about 50 to 90 percent.

In order to minimize the heating energy for the stripping process, the fed in and discharged fermentation residue is pre-heated or, respectively, cooled down (11) in a counter current process. In order to enable the counter current process, three stripping containers are furnished for the stripping process, of which a maximum of two containers are in operation or, respectively, one container is in operation and in each case one container is being filled and emptied. The hygienized fermentation residue low in nitrogen is fed continuously to a separator (13) through a buffer container (12). Alternatively the stripping process can be performed with four stripping containers, wherein in each case one container is filled and one container is emptied and as well two containers are in operation. This variation dispenses with the buffer container (12) disposed in front of the separator (13).

The fermentation residue is separated by the separator (13) in a solid phase and in a liquid phase. The dry substance part of the liquid phase amounts to approximately 2 to 6 percent. The liquid phase is used for mashing the substrate. At the same time a thermal disintegration of the biomass of the fermentation residue is achieved by the stripping process. A further conversion of the recirculated biomass of the liquid phase is achieved thereby in the fermentation container and thus increased gas yields are obtained.

The dry substance part of the solid phase amounts approximately 25 to 50 percent. The ammonium concentration is reduced by the stripping process in the solid phase to about 0.5 to 10 kg NH4/t TS (kg ammonium/ton dry substance). The ammonia emissions are therewith clearly reduced. For comparison the ammonium concentration in untreated liquid fermentation residue amount to about 20 to 80 kg NH4/t TS (kg ammonium/ton dry substance). The odor emissions are reduced by the disintegration of the substrates in the biogas process and by the hygienization. A further aerobic disintegration of the fermentation residue and therewith the generation of odor emissions is prevented by the air drying of the fermentation residue with the discharge heat (14) from the stripping process. The solid fermentation residue is stored and can be brought out in agriculture as a fertilizer.

The biogas process has to be heated. Based on the mass ratios between substrate and recirculated liquid there occurs the essential heat input into the biogas process by the stripping process. Furthermore, the waste heat of the stripping process is employed for heating of the biogas process. Alternatively, the heat of the power heat coupling plant (20) can directly be employed for heating. The heating is performed by an external heat exchanger (18). For this purpose the substrate is removed from the pre-stage and the fermentation containers, is heated up in the heat exchanger and is pumped back. The containers are alternatingly heated up and the substrate is again fed to the container from which it had been taken. The substrate for heating is removed at the output of the cyclone in order to keep the dirt carried and therewith also the soiling of the heat exchanger as low as possible.

The method according to the FIG. 3 will be formed as a variation to the circuit in FIG. 2. The biological pre-stage (7) and the sand separation (23) are separated in apparatus technology in this variation. The substrate is subjected to a substrate regeneration (10) after the biological pre-stage (7). The substrate regeneration is performed in the same way as the previously described variation.

The hygienized and low nitrogen substrate is fed to the interfering material separator (23). As an alternative to FIG. 3, the interfering material separator (23) can also be disposed between the substrate regeneration (10) and the counter current heat exchanger (11). The substrate, which is hygienized and freed from retarding materials and interfering materials, is fed from the interfering material separator to the successively following fermentation containers (8,9) for biogas formation. The fermentation is performed as described above. The fermentation residue of the biogas process (discharge of the fermentation container) is fed to the separator (13) for separating the fermentation residue into a solid phase and into a liquid phase. The liquid phase is employed for mashing the substrate. A recirculation in two part streams can be dispensed with in this variation. The remainder of the method in FIG. 3 remains unchanged in comparison with the method according to FIG. 2.

As a further variation the removal of the interfering materials both after the biogas obtaining (FIG. 2) as well as also after the hydrolysis (FIG. 3) results in accomplishing a particular high degree of separation relative to the retarding materials.

EMBODIMENT EXAMPLE

The example for the performance of the method employs chicken dung as a substrate, however the example is also suitable for demonstrating the use of all other already recited substrates with high nitrogen or high solid parts (compare drawing balance FIG. 4). The use of chicken dung is characterized in that this substrate exhibits a high dry substance part (dry substance TS=30% to 80%) and a high nitrogen part of up to 6% of the dry substance TS. In the present example calculation the dry substance part amounts to 48% with a nitrogen part of 5% of the dry substance TS.

In modification of the described method the chicken dung is fed directly to the pre-stage without comminution and mixing. A pumpable substrate with a dry substance part of TS=10% to 15% is generated by mashing with recirculation liquid. According to an example calculation, the dry substance part amounts to 12.5 percent, wherein about 2,000 t recirculate or, respectively, at the first start-up such an amount of water are required. The mixing is performed by the central stirring system of the cyclone.

The dwelling time of the substrate in the cyclone amounts to four days in the embodiment example. The sand bound into the chicken dung deposits in the cyclone. According to the example annually about 860 t sand are separated from the process.

The adjustment of the required particle size of the substrate is performed in the successively following in line comminuting machine. Essentially straw and feathers are comminuted in the inline comminuting machine to such an extent that a good pumpability and an interference free flow of substrate in the pipelines are assured by the particle size. A pump successively following to the inline comminuting machine transports the substrate into the fermentation container.

The dwelling time of the substrate in the fermentation containers amounts to 30 days in the application case. The process runs mesophilic at 40 degrees centigrade. The ammonium concentration in the fermentsation container amounts to about 4 kg NH4-N/t substrate.

The generated biogas is re-generated in an external gas purification prior to its use in a block heat power station. An emergency flare and an emergency heating are installed in order to assure the use of the biogas and the heating of the substrate regeneration in case of a failure of the thermal power station. The electric current is fed into the grid, while the heat serves to supply the substrate regeneration and additional users.

After the fermentation the part stream 1 of the fermented substrate is recirculated with the dry substance part of 7.5 percent and is fed again to the mixer. The bacteria necessary for the fermentation are thereby mixed to the new substrate. The residual substrate (part stream 2) is fed to the substrate regeneration. The residual substrate is hygienized there and about 310 t nitrogen are removed annually. Thereupon the separation occurs into a liquid phase and a solid phase. The recirculated liquid phase exhibits still an ammonium concentration of about 0.8 kg NH4-N/t substrate with a dry substance part of three percent. The recirculated liquid phase is employed for the mashing of new substrates just like the part stream 1.

By the mixing of the new substrate with the recirculate of part stream 1 and part stream 2 in the mixer there results a temperature of the mixture of about 36 degrees centigrade. The pre-stage and the fermentation container are heated with the waste heat of the substrate regeneration through a heat exchanger. Here a warming from 36 degrees centigrade to 40 degrees centigrade has to be assured by the heating and the thermal losses of the biogas plant have to be compensated.

The hygienized solid phase of the fermentation residue has a dry substance part of about 36 percent in the application case. After an air drying the hygienized solid phase is stored in the solid material storage with a dry substance part of about 66 percent and can be fed to use, for example in agriculture. Waste heat from the stripping process is employed as heat for the air drying.

The invention is explained in more detail by the following figures:

FIG. 1: principal sketch

FIG. 2: flowchart diagram 1

FIG. 3: flowchart diagram 2

FIG. 4: accounting representation for the embodiment example

The invention exhibits substantial advantages relative to the state of the art. It is now possible to use substrates in accordance with the present invention, where the substrates could not be employed or only with large disadvantages employed in conventional biogas methods.

The economic advantage of the invention is associated amongst others with the lesser use of water in comparison to conventional wet fermentation processes with simultaneously improved biogas generation and therewith clearly increased gas yields in comparison to dry fermentation processes.

Table 2 represents the invention in comparison with a standard wet fermentation. As can be recognized from the table there result by way of example according to the present invention reduced investments for the fermentation residue storage of about 480,000 EURO. Furthermore, the annual costs for the water and the bringing out of the fermentation residues onto agriculturally used areas are reduced by about 458,000 EURO.

TABLE 2

Comparison of the present invention with a conventional wet fermentation

| | Present invention | | | Wet fermentation | | |
|---|---|---|---|---|---|---|
| Chicken dung | 23,000 ton/year | | | 23,000 ton/year | | |
| Water use | 2,000 ton/year | | 4,000 €/year | 51,000 ton/year | 102,000 €/year | |
| Fermentation residual amount | 8,500 ton/year | | | 68.500 ton/year | | |
| Storage space | 8,000 m³ | | 170,000 € | 34,250 m³ | 650,000 € | |
| Costs of bringing out the fermentation residues | 6 €/ton | | 51,000 €/year | 6 €/ton | 411,000 €/year | |

Table 2: Comparison of the present invention with a conventional wet fermentation

REFERENCE CHARACTER LEGEND TO FIG. 1

4 mixing, comminuting
5 mixing, comminuting
7 pre-stage
8 fermentation container
9 gas bubble
10 substrate regeneration
A recirculate part stream 1
AA recirculate part stream 1
B part stream 2
BB recirculate part stream 2
α biomass
β fermentation residue
dotted area aggregate limit of solid materials
crossed lines aggregate limit of liquid materials

REFERENCE CHARACTER LEGEND TO FIG. 2

1 receiver container
2 silo
3 comminuting machine
4 mixer
5 inline comminuting machine
6 pump substrate
7 pre-stage
8 fermentation container
9 gas bubble
10 substrate regeneration
11 heat exchanger substrate regeneration
12 buffer
13 separator
14 fermentation residue drying
15 fermentation residue storage
16 pump re-circulating
17 pump heating
18 heat exchanger heating system
19 gas purification
20 power heat connect plant KWK
21 user
22 process monitoring
A,AA recirculate part stream 1
B part stream 2
BB recirculate part stream 2
Continuous line substrate
pointed line biogas
dash/dash/point/dash/dash recirculate II
dashed line fore-runnings
dash/point/point/dash reflux

The invention claimed is:

1. Method for using of biomass in a biogas process, comminuting initially biomass present as a solid in the comminuting machine, mashing the biomass, inoculating the biomass with bacteria and withdrawing generated biogas,
characterized in that
comminuted biomass is mashed with recirculate in a mixer and the substrate is transferred into a pumpable state, thereupon the pumpable mixture is further homogenized in an inline comminuting machine,
hydrolysis and acid formation based on bacteria interaction run in one or several successively following separators with stirring system,
inorganic components are separated and thrown out,
acetic acid formation and methane generation run in fermentation containers under continuous mixing at increased temperatures, wherein biogas is generated, the biogas is withdrawn, possibly stored, and fed to an energetic use, while the generated fermentation residue is subdivided into two part streams, wherein part stream 1 is not treated and serves for mashing new biomass,
in contrast part stream 2 is subjected to a substrate regeneration,
by withdrawing from part stream 2 ammonia/ammonium nitrogen in a stripping process, wherein the part stream 2 is warmed possibly by way of heat exchanger after the stripping process,
and part stream 2 now is fed continuously to a separator through a buffer container as a hygienized and low nitrogen fermentation residue and is separated into a solid phase and a liquid phase,
wherein the liquid phase is fed as a recirculate to the mixer, therein the solid phase either is dried or employed as a suspension, and,
further characterized in that according to FIG. 2
comminuted biomass is mashed with recirculate in a mixer (4) and the substrate is transferred into a pumpable state, successively following the pumpable mixture is further homogenized in an inline comminuting machine (5),
hydrolysis and acid formation are running by bacterial interaction in one or several successively connected cyclones with a central stirring system (7),
inorganic components are separated and discarded,
acetic acid formation and methane generation run in fermentation containers (8) under continuous mechanical intermixing at a temperature of approximately 40 degrees centigrade, wherein biogas is generated,
the biogas is withdrawn, stored (9) and fed to an energetic use in a power heat coupling plant KWK (20),
while generated fermentation residues are separated into two part streams, wherein part stream 1 (A,AA), which exhibits a temperature of about 40 degrees centigrade, remains untreated and serves for mashing new biomass, in contrast part stream 2 (B) is subjected to a substrate regeneration (10), heating the part stream 2 (B) to about 70 to 90 degrees centigrade, withdrawing ammonia/ammonium nitrogen in the stripping process from the part stream 2 (B), wherein the necessary heat for this stripping process comes from the power heat coupling plant KWK (20), wherein the stripping process itself runs at a temperature of about 75 to 90 degrees centigrade, the fed in and led away fermentation residue is cooled or, respectively, preheated in the counter current method (11), the part stream 2 as a now hygienized and low nitrogen fermentation residue is continuously fed to a separator (13) through a buffer container (12) after the stripping process through the heat exchanger (11) with a temperature of about 45 degrees centigrade and the part stream to is separated into a solid phase and a liquid phase, the liquid phase is fed to the mixer (4) as a recirculate (BB), the solid phase is either dried (14) or directly employed as a suspension for fertilizer in agriculture, or further characterized in that according to FIG. 3 comminuted biomass is mashed with recirculate in a mixer (4) and the substrate is transferred into a pumpable state, thereupon the pumpable mixture is further homogenized in an inline comminuting machine (5), hydrolysis and acid formation run based on bacterial interaction in one or several successively connected prestages (7) with a central stirring system, the generated suspension is thereupon to a substrate regeneration (10), by heating the suspension to 70 to 90 degrees centigrade, wherein ammonia/ammonium nitrogen are withdrawn from the suspension in a stripping process, wherein the required heat for the stripping process can come from the power heat coupling plant KWK (20), wherein the stripping process runs at a temperature of from 70 to 90 degrees centigrade, the fed in and led away fermentation residue is cooled or, respectively, preheated in the counter current method (11), inorganic components are separated and discarded in a separator (23), formation of acetic acid and generation of methane run in fermentation containers (8) with continuous mixing at a temperature from 30 to 60 degrees centigrade, the biogas is withdrawn, stored (9), and led to an energetic use, the now homogenized and low in nitrogen fermentation residues are continuously fed to a separator (13) and are separated into a solid phase and a liquid phase, wherein the liquid phase is fed to the mixer (4) as a recirculate, wherein the solid phase is either dried (14) or directly employed as a suspension.

2. Method for using biomass in a biogas process according to claim 1, characterized in that according to FIG. 2 comminuted biomass is mashed with recirculate in a mixer (4) and the substrate is transferred into a pumpable state, successively following the pumpable mixture is further homogenized in an inline comminuting machine (5), hydrolysis and acid formation are running by bacterial interaction in one or several successively connected cyclones with a central stirring system (7), inorganic components are separated and discarded, acetic acid formation and methane generation run in fermentation containers (8) under continuous mechanical intermixing at a temperature of approximately 40 degrees centigrade, wherein biogas is generated, the biogas is withdrawn, stored (9) and fed to an energetic use in a power heat coupling plant KWK (20), while generated fermentation residues are separated into two part streams, wherein part stream 1 (A,AA), which exhibits a temperature of about 40 degrees centigrade, remains untreated and serves for mashing new biomass, in contrast part stream 2 (B) is subjected to a substrate regeneration (10), heating the part stream 2 (B) to about 70 to 90 degrees centigrade, withdrawing ammonia/ammonium nitrogen in the stripping process from the part stream 2(B), wherein the necessary heat for this stripping process comes from the power heat coupling plant KWK (20), wherein the stripping process itself runs at a temperature of about 75 to 90 degrees centigrade, the fed in and led away fermentation residue is cooled or, respectively, preheated in the counter current method (11), the part stream 2 as a now hygienized and low nitrogen fermentation residue is continuously fed to a separator (13) through a buffer container (12) after the stripping process through the heat exchanger (11) with a temperature of about 45 degrees centigrade and the part stream to is separated into a solid phase and a liquid phase, the liquid phase is fed to the mixer (4) as a recirculate (BB), the solid phase is either dried (14) or directly employed as a suspension for fertilizer in agriculture.

3. Method for using of biomass in a biogas process according to claim 1, characterized in that according to FIG. 3 comminuted biomass is mashed with recirculate in a mixer (4) and the substrate is transferred into a pumpable state, thereupon the pumpable mixture is further homogenized in an inline comminuting machine (5), hydrolysis and acid formation run based on bacterial interaction in one or several successively connected prestages (7) with a central stirring system, the generated suspension is thereupon subjected to a substrate regeneration (10), by heating the suspension to 70 to 90 degrees centigrade, wherein ammonia/ammonium nitrogen are withdrawn from the suspension in a stripping process, wherein the required heat for the stripping process can come from the power heat coupling plant KMK (20), wherein the stripping process runs at a temperature of from 70 to 90 degrees centigrade, the fed in and led away fermentation residue is cooled or, respectively, preheated in the counter current method (11), inorganic components are separated and discarded in a separator (23), formation of acetic acid and generation of methane run in fermentation containers (8) with continuous mixing at a temperature from 30 to 60 degrees centigrade, the biogas is withdrawn, stored (9), and led to an energetic use, the now homogenized and low in nitrogen fermentation residues are continuously fed to a separator (13) and are separated into a solid phase and a liquid phase, wherein the liquid phase is fed to the mixer (4) as a recirculate, wherein the solid phase is either dried (14) or directly employed as a suspension.

4. Method according to claim 1,
characterized in that during start-up of the continuous biogas process water or liquid manure are employed for mashing instead of the fermentation residue.

5. Method according to claim 1,
characterized in that the dwelling time in the pre-stage amounts to from one to six days.

6. Method according to claim 1,
characterized in that with the part stream 1 the substrate in the mixer (4) or in the fermentation container (8) is bacterially inoculated.

7. Method according to claim 1,
characterized in that the fermentation in the fermentation container (8) is performed mesophilic at temperatures between 35 and 42 degrees centigrade or thermophilic at temperatures between 50 and 60 degrees centigrade.

8. Method according to claim 1,
characterized in that in several fermentation containers (8) it is operated mesophilic and thermophilic independent of each other and that the dwelling time in the fermentation containers (8) amounts to from 20 to 40 days.

9. Method according to claim 1,
characterized in that the stripping process runs at a temperature above 70 degrees centigrade and for a time period of more than one hour as a batch process.

10. Method according to claim 1,
characterized in that the stripping process runs in a thermal counter current method relative to the fermentation residue feed in and discharge.

11. Method according to claim 1,
characterized in that of three stripping containers in each case one is filled and operated and emptied or one is empty and two are operated, that of four stripping containers in each case one is being filled and emptied and two are operated and the buffer container is dispensed with.

12. Method according to claim 1,
characterized in that the pre-stage (7) and the fermentation container (8) is warmed and that the solid phase in the fermentation residues college (15) is dried by heating with the residual heat from this stripping process.

13. Method according to claim 1,
characterized in that poultry dung is used as the biomass with high foreign material part, that the poultry dung is fed immediately to the pre-stage (7), the mixing through is performed at the pre-stage (7) and the mixture is thereupon fed to the inline comminuting machine.

\* \* \* \* \*